(12) United States Patent
Nielsen et al.

(10) Patent No.: US 8,075,480 B2
(45) Date of Patent: Dec. 13, 2011

(54) APPARATUS FOR REDUCING CROSS-CONTAMINATION

(75) Inventors: Per Gorm Gunther Nielsen, North Rocks (AU); Michael Gunther Nielsen, North Rocks (AU)

(73) Assignees: Techmin Pty Limited, New South Wales (AU); Sydney West Area Health Service, New South Wales (AU)

( * ) Notice: Subject to any disclaimer, the term of this patent is extended or adjusted under 35 U.S.C. 154(b) by 424 days.

(21) Appl. No.: 12/085,475

(22) PCT Filed: Nov. 21, 2006

(86) PCT No.: PCT/AU2006/001752
§ 371 (c)(1),
(2), (4) Date: Feb. 9, 2009

(87) PCT Pub. No.: WO2007/059564
PCT Pub. Date: May 31, 2007

(65) Prior Publication Data
US 2009/0270684 A1    Oct. 29, 2009

(30) Foreign Application Priority Data
Nov. 25, 2005    (AU) ............................... 2005906602

(51) Int. Cl.
*A61B 1/267* (2006.01)
(52) U.S. Cl. ........................................................ 600/185
(58) Field of Classification Search .......... 600/185–200; 292/80; 285/376, 401, 402; 403/348, 349
See application file for complete search history.

(56) References Cited

U.S. PATENT DOCUMENTS

| | | | |
|---|---|---|---|
| 5,554,166 A | 9/1996 | Lange | |
| 5,702,351 A * | 12/1997 | Bar-Or et al. | 600/190 |
| 5,879,304 A * | 3/1999 | Shuchman et al. | 600/193 |
| 6,102,851 A | 8/2000 | Mellin | |
| 2002/0087050 A1 | 7/2002 | Rudischhauser et al. | |
| 2003/0018239 A1 | 1/2003 | Cartledge et al. | |
| 2004/0215062 A1 | 10/2004 | Dalle et al. | |
| 2004/0260325 A1* | 12/2004 | Kuhr et al. | 606/181 |
| 2004/0267254 A1 | 12/2004 | Manzo et al. | |

FOREIGN PATENT DOCUMENTS

| | | |
|---|---|---|
| AU | 2003255212 | 11/2003 |
| AU | 2007216622 | 9/2007 |
| WO | WO 97/17885 | 5/1997 |
| WO | WO 9717885 | 5/1997 |
| WO | WO 02/071930 | 9/2002 |

* cited by examiner

*Primary Examiner* — Eduardo C Robert
*Assistant Examiner* — Nicholas Plionis
(74) *Attorney, Agent, or Firm* — Cozen O'Connor

(57) ABSTRACT

A re-use prevention mechanism (160) for an apparatus (110) having a reusable part (120) and a single-use disposable part (130) connectable to the reusable part (120) is disclosed. The re-use prevention mechanism (160) comprises a blocking portion (1603) disposed, in use, between the disposable part (130) and the reusable part (120). An actuating member (1605) is operable between the blocking portion (1603) and one of the disposable part (130) and the reusable part (120) for moving the blocking portion (1603) into a blocking position upon disconnection of the disposable part (130) from the reusable part (120). hi the blocking position, the blocking portion (1603) engages an abutment surface (1206) on one of the disposable part (130) and the reusable part (120) if a user attempts to reconnect the disposable part (130) to the reusable part (120) and thereby prevents re-connection of the disposable part (130) to the reusable part (120).

20 Claims, 11 Drawing Sheets

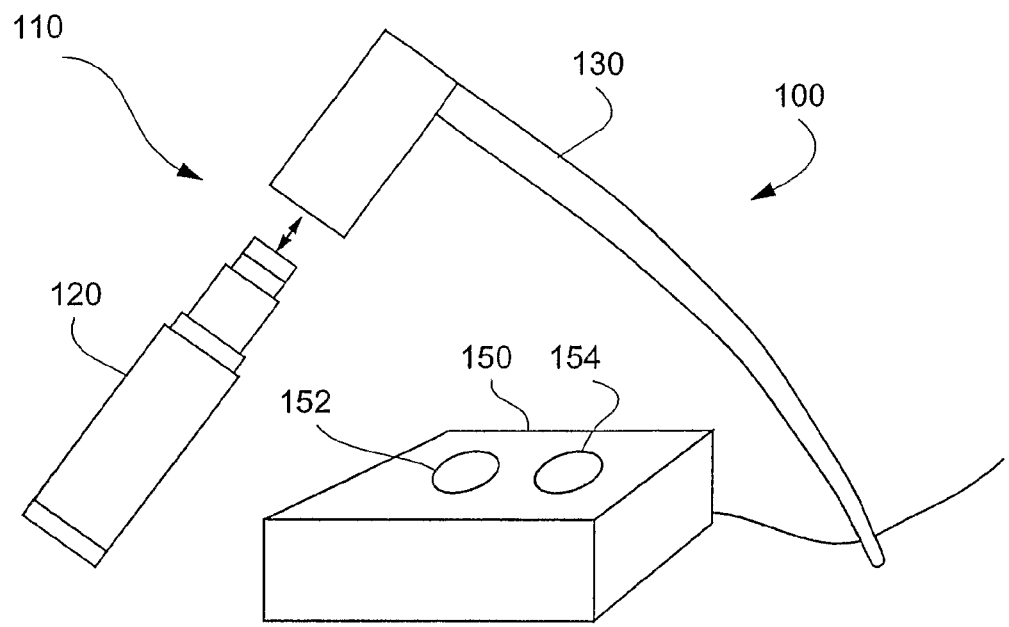
Fig. 1
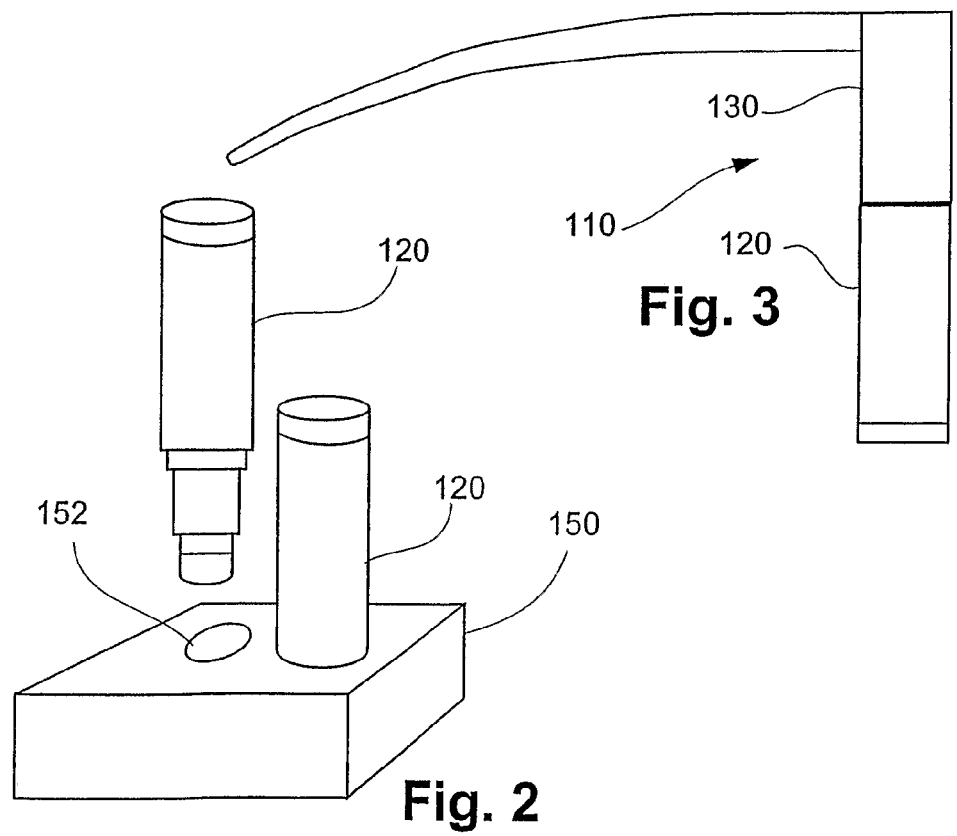
Fig. 2
Fig. 3

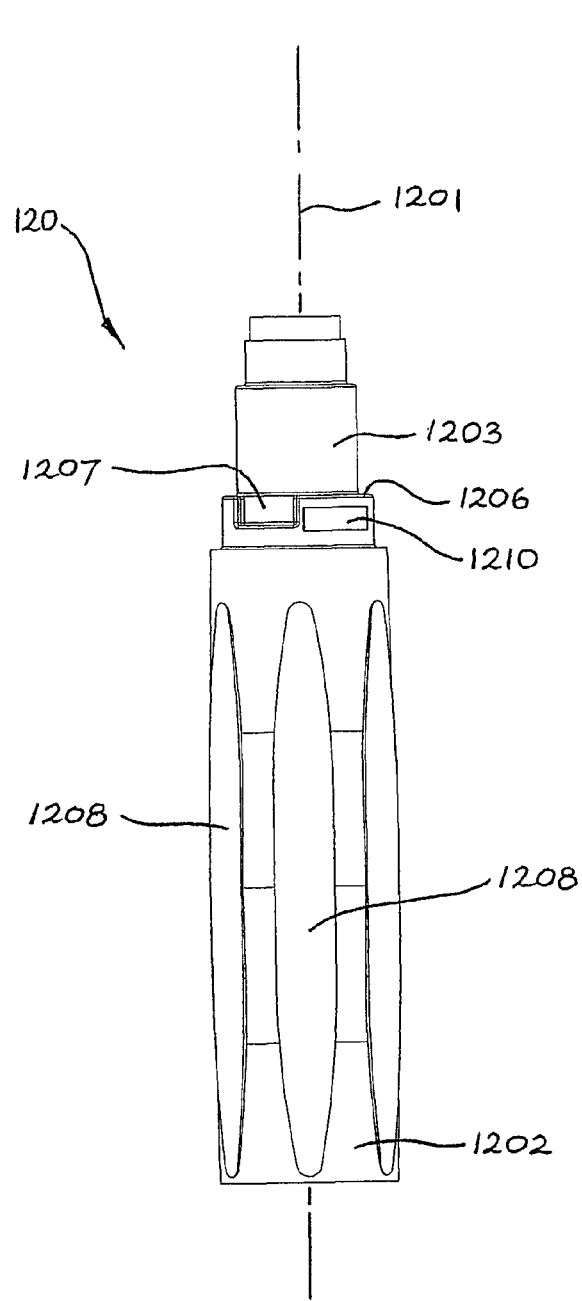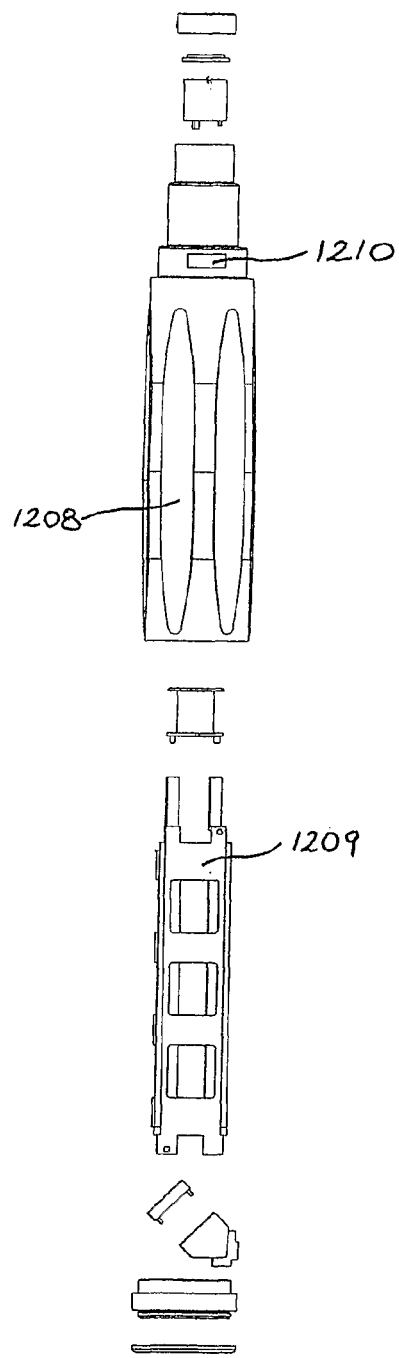
FIG. 4
FIG. 5

APPARATUS FOR REDUCING CROSS-CONTAMINATION

PRIORITY CLAIM

This is a U.S. national stage of application No. PCT/AU2006/001752, filed on Nov. 21, 2006. Priority is claimed on the following application(s): Country: Australia, Application No.: 2005906602, Filed: Nov. 25, 2005, the content of which is incorporated here by reference.

FIELD OF THE INVENTION

The invention relates generally to improvements in apparatus for reducing cross-contamination, and more particularly to a re-use prevention mechanism and to a laryngoscope.

While the invention has been developed primarily for use in laryngoscopes, and will be described hereinafter with reference to this application, it will be appreciated that the invention is not limited to this particular application and may also be used, for example, in other medical instruments, such as endoscopes and catheters, or indeed, in non-medical applications where hygiene is important, for example in electric toothbrushes with disposable heads, to reduce the incidence of cross-infection or contamination resulting from re-use of disposable parts.

BACKGROUND OF THE INVENTION

Known laryngoscopes comprise an elongate handle and an arcuate blade that is adapted for insertion into a patient's throat. The blade is connected to the handle by rotating the blade upwardly with respect to the handle. The handle is hollow and contains batteries for powering a light source to provide illumination to a distal end of the blade.

Historically, the handle and blade have been formed from metal to provide the stiffness required for opening a patient's airway. Accordingly, these known laryngoscopes have a high capital cost, and are therefore sterilised and reused many times during their service life. The typical cleaning method is autoclaving, which is in itself expensive.

In recent years, concern has been raised as to the adequacy of the cleaning and sterilisation of laryngoscopes. It is noted that metal laryngoscope handles are particularly difficult to clean, as they are often knurled, which provides a multitude of locations for bacteria and other contaminants to avoid sterilisation. In an attempt to address this problem, some disposable blade laryngoscopes have been developed. However, known disposable blade laryngoscopes have retained the same connection system as for the older fully reusable metal laryngoscopes, in that the blade is rotated upwardly with respect to the handle to engage the blade to the handle. When the disposable blades are connected to the handle in this manner, the blade tip often touches the handle, and accordingly, contaminants present on the handle can be transferred to the blade and subsequently to the patient.

Another problem with known disposable blades is that they often lack means for preventing their accidental re-use. Where means for preventing blade re-use are provided, it is often only apparent after a user has attempted several times to connect the blade to the handle that the blade in hand is a used blade, thereby causing user frustration and time delays. As will be appreciated, such frustration and delays can be critical in many instances where laryngoscopes are required.

OBJECT OF THE INVENTION

It is an object of the present invention to overcome or substantially ameliorate one or more of the abovementioned disadvantages of the prior art, or at least to provide a useful alternative.

SUMMARY OF THE INVENTION

Accordingly, in a first aspect, the present invention provides a re-use prevention mechanism for an apparatus having a reusable part and a single-use disposable part connectable to the reusable part, the re-use prevention mechanism comprising:

a blocking portion disposed, in use, between the disposable part and the reusable part;

an actuating member operable between blocking portion and one of the disposable part and the reusable part for moving the blocking portion into a blocking position upon disconnection of the disposable part from the reusable part;

wherein, in the blocking position, the blocking portion engages an abutment surface on one of the disposable part and the reusable part if a user attempts to reconnect the disposable part to the reusable part and thereby prevents re-connection of the disposable part to the reusable part.

In a second aspect, the invention provides medical device comprising:

a reusable part defining a longitudinal axis;

a disposable part for connection to the reusable part by engaging the disposable part with a longitudinal end of the reusable part and rotating the disposable part relative to the reusable part about the longitudinal axis.

Preferably, the medical device further includes a re-use prevention comprising:

a blocking portion disposed, in use, between the disposable part and the reusable part;

an actuating member operable between blocking portion and one of the disposable part and the reusable part for moving the blocking portion into a blocking position upon disconnection of the disposable part from the reusable part;

wherein, in the blocking position, the blocking portion engages an abutment surface on one of the disposable part and the reusable part if a user attempts to reconnect the disposable part to the reusable part and thereby prevents re-connection of the disposable part to the reusable part.

Preferably, according to either of the above aspects, the actuating member is operable between the blocking member and the disposable part. More preferably, the actuating member resiliently biases the blocking portion toward the blocking position upon disconnection of the disposable part from the reusable part.

In a preferred form, when the disposable part is engaged with the distal end of the reusable part, the blocking portion engages a recess in the reusable part to rotationally lock the disposable part to the reusable part.

Preferably, the reusable part is elongate and defines a longitudinal axis. More preferably, the actuating member resiliently biases the blocking portion rotationally, about the longitudinal axis, toward the blocking position upon disconnection of the disposable part from the reusable part.

Preferably, the disposable part is adapted for connection to the reusable part by engaging the disposable part with a longitudinal end of the reusable part and rotating the disposable part relative to the reusable part about the longitudinal axis. More preferably, the reusable part is generally cylindrical and includes a pair of locking lugs extending radially outwardly from diametrically opposite sides thereof. In a preferred form, the disposable part includes a generally cylindrical tubular coupling sleeve that is adapted to longitudinally slidably engage over a distal end of the reusable part. The disposable part preferably includes a pair of locking flanges extending radially inwardly from diametrically opposite sides of the sleeve and adapted to engage the locking lugs upon rotation, about the longitudinal axis, of the disposable part relative to the reusable part.

Preferably, engagement of the blocking portion with the abutment surface limits the extent of longitudinal engagement of the disposable part with the reusable part to prevent engagement of the locking lugs and locking flanges. More preferably, a longitudinally extending recess is provided in said one of the disposable part and the reusable part, the blocking portion being engageable with the recess to permit sufficient longitudinal engagement of the disposable part with the reusable part to allow the locking lugs and locking flanges to engage.

In a preferred form, the disposable part includes a cylindrical coupling sleeve adapted to engage the reusable part. Preferably, the re-use prevention mechanism is, in use, located in the cylindrical coupling sleeve.

Preferably, the re-use prevention mechanism includes first and second interengageable collars connectable with one of the disposable part and the reusable part, the collars being rotatably lockable to one another in first and second relative rotational positions, wherein the blocking member extends from one of the collars, and wherein in the first position if a user attempts to connect the disposable part to the reusable part, the blocking portion engages the recess, and wherein in the second position if a user attempts to connect the disposable part to the reusable part, the blocking portion engages the abutment surface. In a preferred form, the collars are connected to the disposable part. More preferably, the blocking portion extends from the first collar.

Preferably, the second collar includes a locking pin for engagement with a corresponding locking aperture in the disposable part to prevent relative rotation of the first collar and the disposable part when the pin and aperture are engaged. The locking pin is preferably adapted to fail if a torque above a predetermined level is applied between the disposable part and the reusable part. Preferably, the locking pin is adapted to withstand a shear force of between around 5 N and around 100 N, more preferably, between around 30 N and around 70 N, and in a particularly preferred form, of around 45 N.

Preferably, the actuating member takes the form of a resilient biasing finger extending longitudinally outwardly from the second collar, away from the reusable part, for engagement with an abutment portion on the disposable part to resiliently bias the second collar rotationally, about the longitudinal axis, with respect to the disposable part when the biasing finger is deformed against the abutment portion. The resilient biasing finger is preferably deformed against the abutment portion when the disposable part is rotated relative to the reusable part to disconnect the disposable part from the reusable part.

Preferably, the reuse prevention mechanism is captivity retained within the coupling sleeve of the disposable part. In a preferred form, the first collar includes a radially outwardly extending retaining lug engageable with a corresponding retaining groove in the disposable part for captivity retaining the reuse prevention mechanism within the coupling sleeve of the disposable part.

Preferably, the second collar includes at least one locking detent engageable with a corresponding notch in the first collar for locking the first and second collars against relative rotation about the longitudinal axis. More preferably, the locking detent engages the notch when the collars are in the second position. In a preferred form, the second collar includes three locking detents and the first collar includes three corresponding notches. Preferably, corresponding pairs of said detents and notches are unevenly circumferentially spaced about said re-use prevention mechanism.

Preferably, the collars permanently lock together when moved into the second position.

The second collar preferably includes a circumferential slot and the first collar preferably includes a corresponding radially extending guide projection engageable with the slot. More preferably, a first end of the slot defines the first position and a second end of the slot defines the second position. Preferably, a stop member is provided at the first end of the slot, the stop member being engageable by the guide projection to retain the collars in the first position. The guide projection is preferably disengageable from the stop member by applying a longitudinal compressive force between the disposable part and the reusable part to cause the guide projection to ride over the stop member.

A longitudinally extending opening preferably extends from one longitudinal end of the second collar and into the slot. Preferably, the guide projection is longitudinally slidably engageable with the longitudinal opening to facilitate interengagement of the first and second collars. In a preferred form, the second collar includes three slots and three corresponding longitudinal openings, and the first collar includes three corresponding guide projections. More preferably, the guide projections and longitudinal openings are unevenly circumferentially spaced about the re-use prevention mechanism, such that the first and second collars can only be interengaged in a single predetermined relative rotational orientation.

Preferably, with the collars in the first position, the disposable part can be axially slid onto the longitudinal end of the reusable part. More preferably, when the disposable part is engaged with the distal end of the reusable part and the disposable part is rotated relative to the reusable part in a predetermined direction, the collars are moved into the second position and the disposable part is locked to the reusable part in a configuration for use.

BRIEF DESCRIPTION OF THE DRAWINGS

A preferred embodiment of the present invention will be described hereinafter, by way of an example only, with reference to the accompanying drawings, in which:

FIG. 1 is a schematic view of a laryngoscope system;

FIG. 2 a schematic view showing how the laryngoscope handle is mounted on the battery charging module;

FIG. 3 is a schematic view of the laryngoscope shown in FIG. 1, wherein the laryngoscope blade and handle are connected for use;

FIG. 4 is a side elevation view of the laryngoscope handle of the system of FIG. 1;

FIG. 5 is an exploded side elevation view of the laryngoscope handle of FIG. 4;

DETAILED DESCRIPTION OF THE PREFERRED EMBODIMENT

Laryngoscope System

Figure 8:
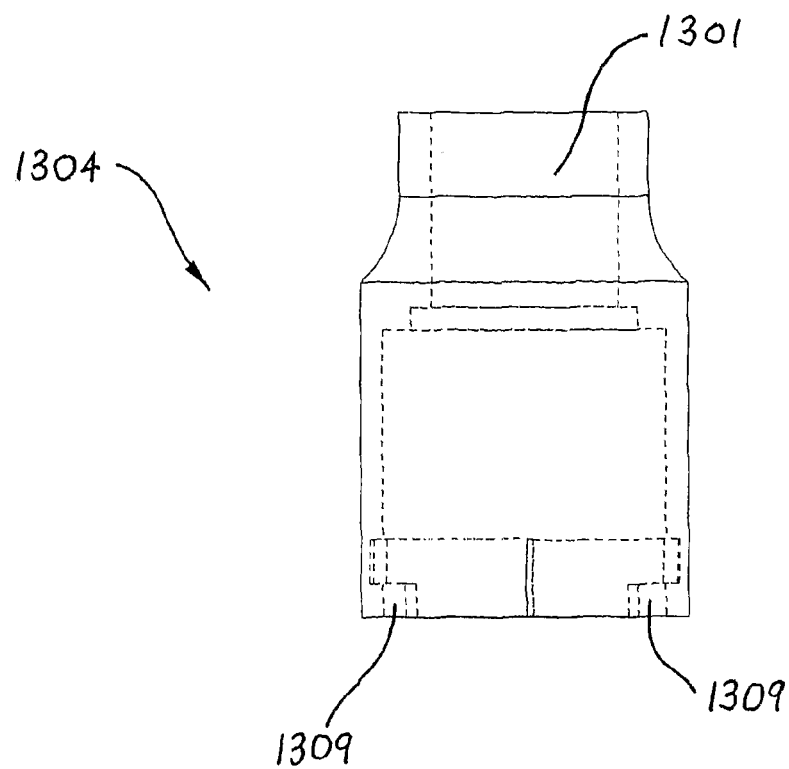
FIG. 8 is an enlarged view of the proximal end of the laryngoscope blade of FIG. 7.

Referring to the drawings, and in particular to FIGS. 1 to 3, there is provided a laryngoscope system 100 comprising a laryngoscope 110 including a reusable handle 120 and a single-use disposable blade 130, as well as a battery charging module 150.

Laryngoscope Handle

Figure 6:
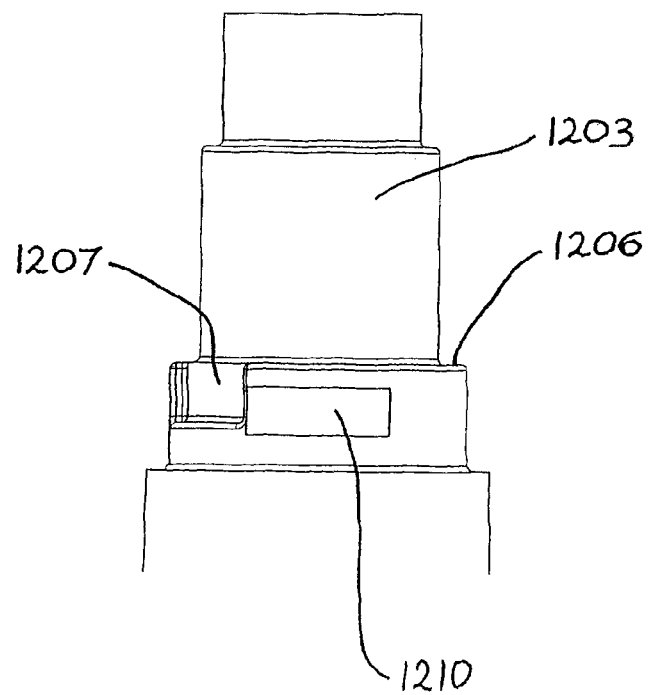
FIG. 6 is an enlarged side elevation view of the distal end of the laryngoscope handle of FIG. 5.

As shown in FIGS. 4, 5 and 6, the handle 120 is generally cylindrical and elongate to define a longitudinal axis 1201, a proximal end 1202 and a distal end 1203.

As can best be seen in FIG. 6, the handle 120 is stepped radially inwardly near its distal end 1203 to define a circumferential annular abutment surface 1206. A recess 1207 extends longitudinally from the abutment surface 1206 toward the proximal end 1202 of the handle 120. The recess 1207 defines a gap in the abutment surface 1206.

Referring again to FIGS. 4 and 5, the peripheral surface of the handle 120 is provided with longitudinally extending contoured lands 1208 to increase surface friction. The smooth contouring of the lands 1208 allows for ease of cleaning of the handle 120.

The handle 120 is hollow and includes an internal mounting frame 1209 to retain rechargeable batteries (not shown).

Laryngoscope Blade

Figure 7:
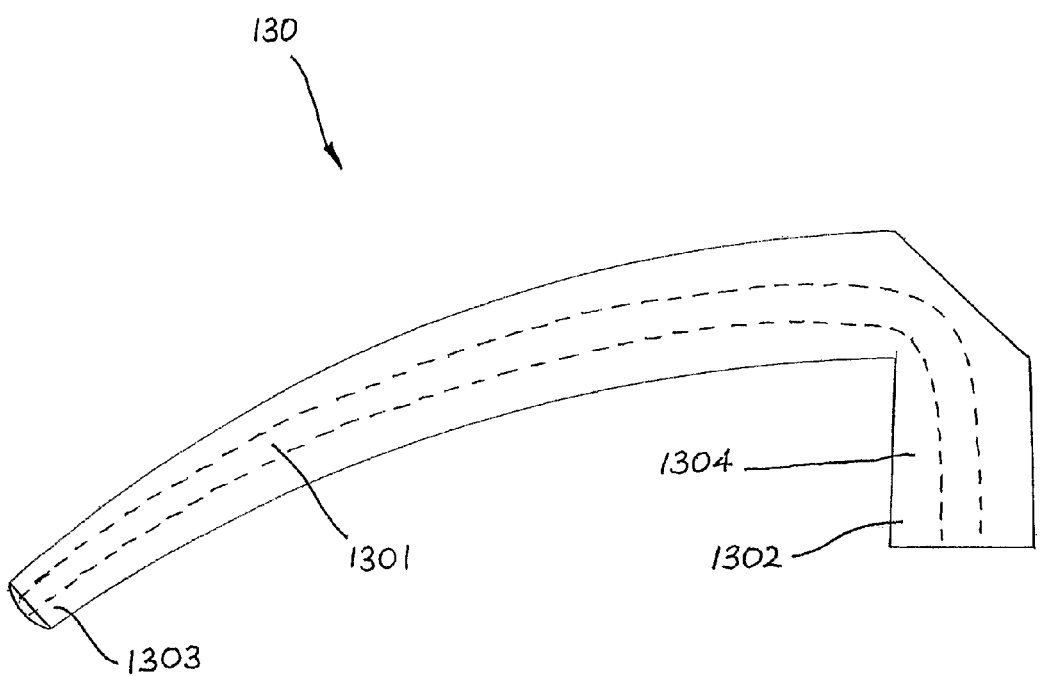
FIG. 7 is a side elevation view of the laryngoscope blade of the system of FIG. 1.

As seen in FIG. 7, the blade 130 is generally arcuate in shape for facilitating its insertion into the throat of a patient. A light pipe 1301 extends from a proximal end 1302 to a distal tip 1303 of the blade 130 for providing illumination into the patient's throat. The light pipe 1301 transmits illumination from a Light Emitting Diode (LED) (not shown) in the end of the handle 120. A suitable light pipe 1301 is disclosed in the Applicants' earlier International Patent Publication No. WO2002/071930, the disclosure of which is incorporated herein in its entirety.

Figure 9:
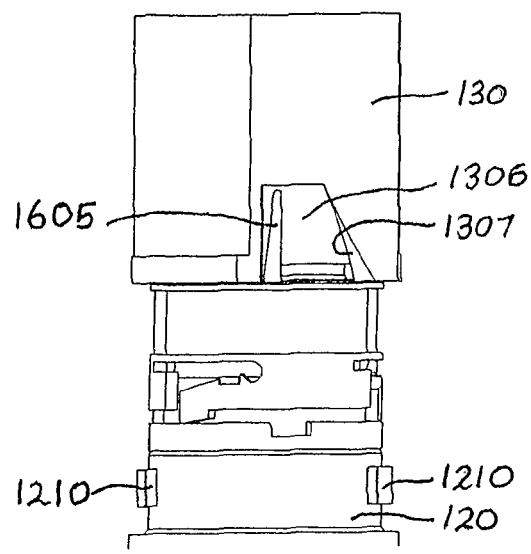
FIG. 9 is a partial side elevation view of the laryngoscope in a partly assembled state, with the coupling sleeve of the blade cut-away to show the re-use prevention mechanism in the first position.
Figure 10:
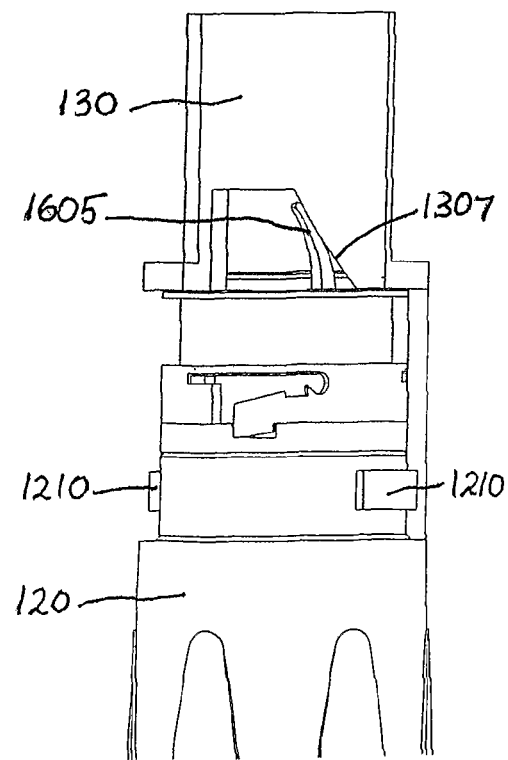
FIG. 10 is a partial side elevation view of the laryngoscope, with the coupling sleeve of the blade cut-away to show the re-use prevention mechanism in a configuration for removal of the blade from the handle.
Figure 11:
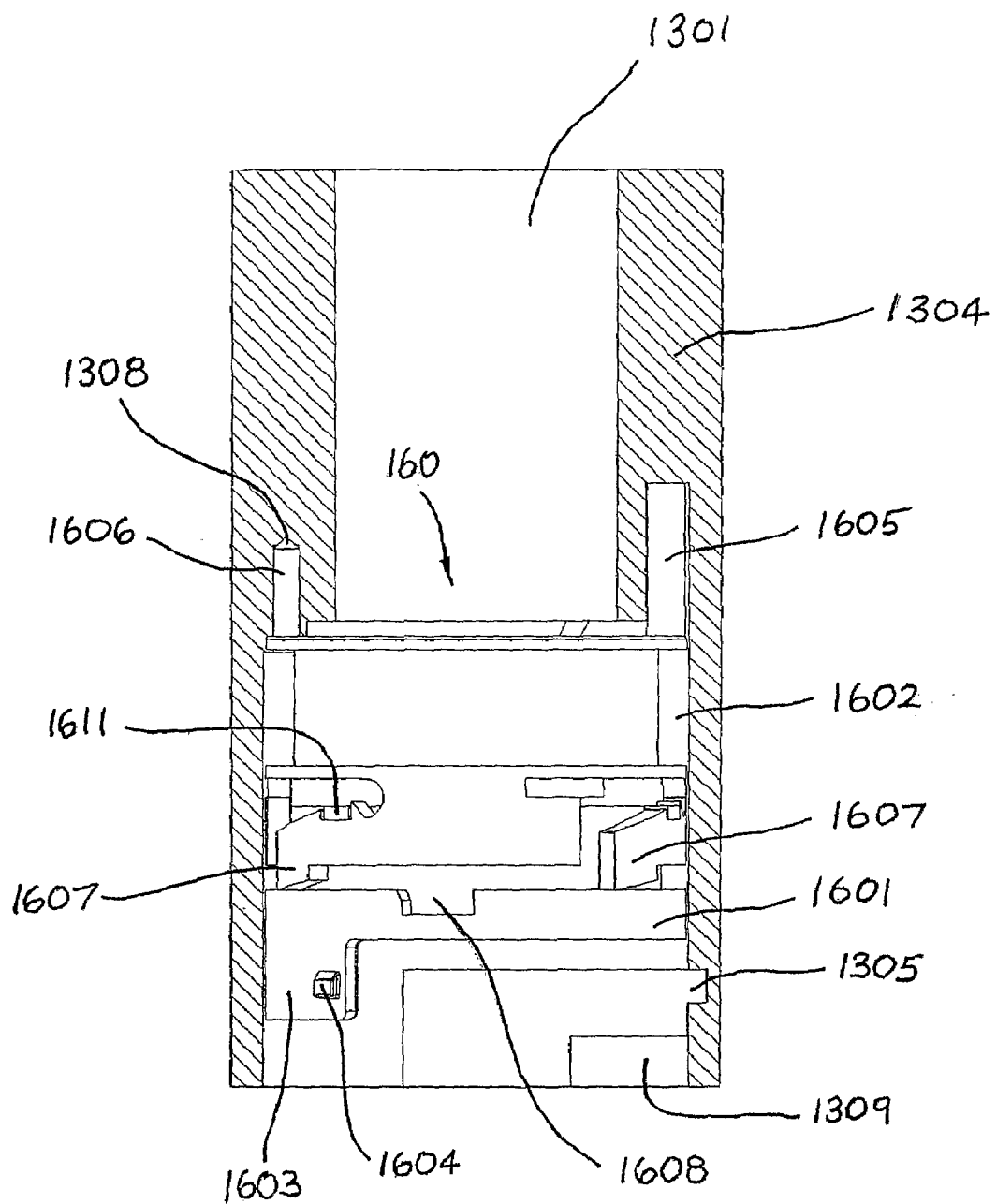
FIG. 11 is a longitudinal section view through the proximal end of the blade of FIG. 8, shown with the re-use prevention mechanism of FIG. 10 installed in the first position.

As best seen in FIG. 8, a generally cylindrical tubular coupling sleeve 1304 is provided at the proximal end 1302 of the blade 130 to facilitate connection of the blade 130 to the handle 120. The coupling sleeve 1304 is configured so as to be longitudinally slidably engageable over the distal end 1203 of the handle 120. As shown in FIGS. 9 and 10, a generally trapezoidal cut-out portion 1306 is provided in a wall of the coupling sleeve 1304. The cut-out portion 1306 defines a radially extending abutment portion 1307 that is oriented diagonally with respect to the longitudinal axis 1201. A longitudinally extending locking aperture 1308 is provided in the proximal end of the coupling sleeve 1304, as can be seen in FIG. 11.

Blade/Handle Coupling

Figure 12:
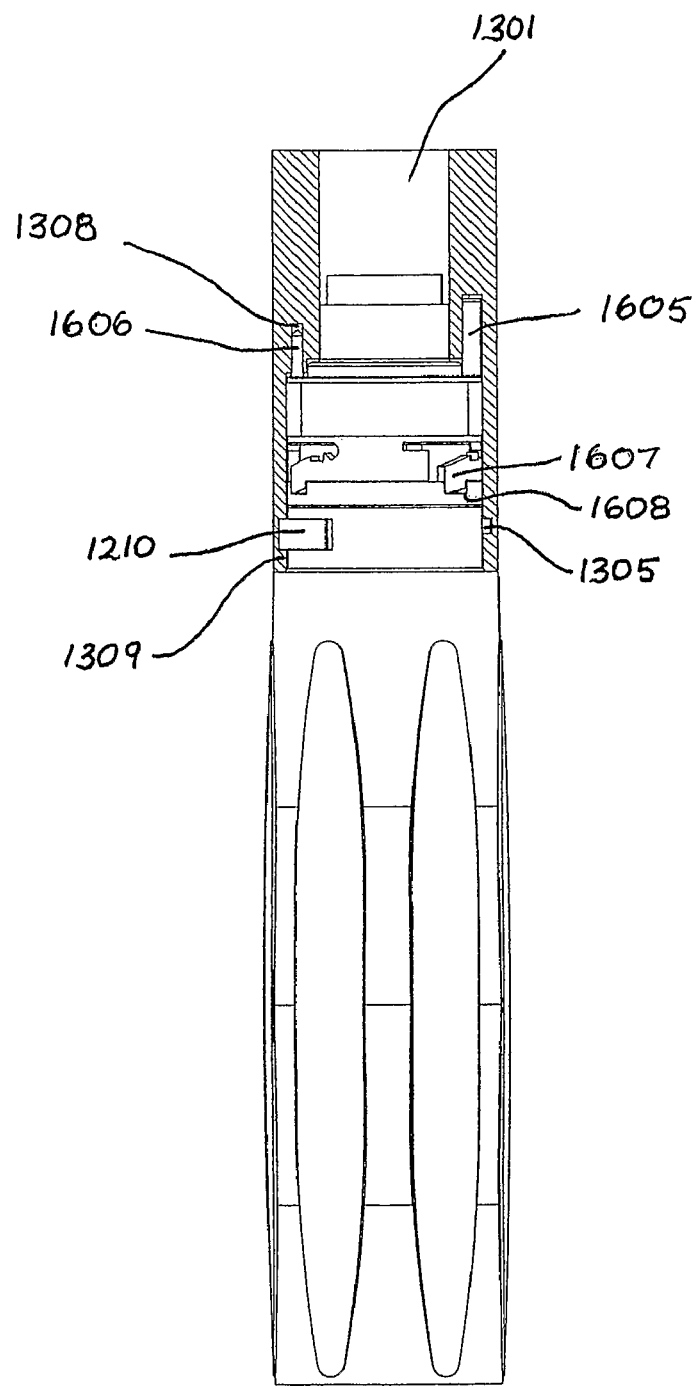
FIG. 12 is a part sectional side elevation view of the assembled handle and blade of the laryngoscope of FIG. 3, showing the re-use prevention mechanism in the second position.

Referring again to FIGS. 4, 5 and 6, the handle 120 includes a pair of locking lugs 1210 that extend radially outwardly from diametrically opposite sides of thereof. The blade 130, as best seen in FIGS. 8, 11 and 12, includes a corresponding pair of locking flanges 1309 that extend radially inwardly from diametrically opposite sides of the to coupling sleeve 1304 for rotational engagement with the locking lugs 1210. The locking flanges 1309 are adapted to engage the locking lugs 1210 upon rotation, about the longitudinal axis 1201, of the blade 130 relative to the handle 120 in order to secure the blade 130 to the handle 120 against relative axial displacement, as shown in FIG. 12.

Re-Use Prevention Mechanism

Figure 14:
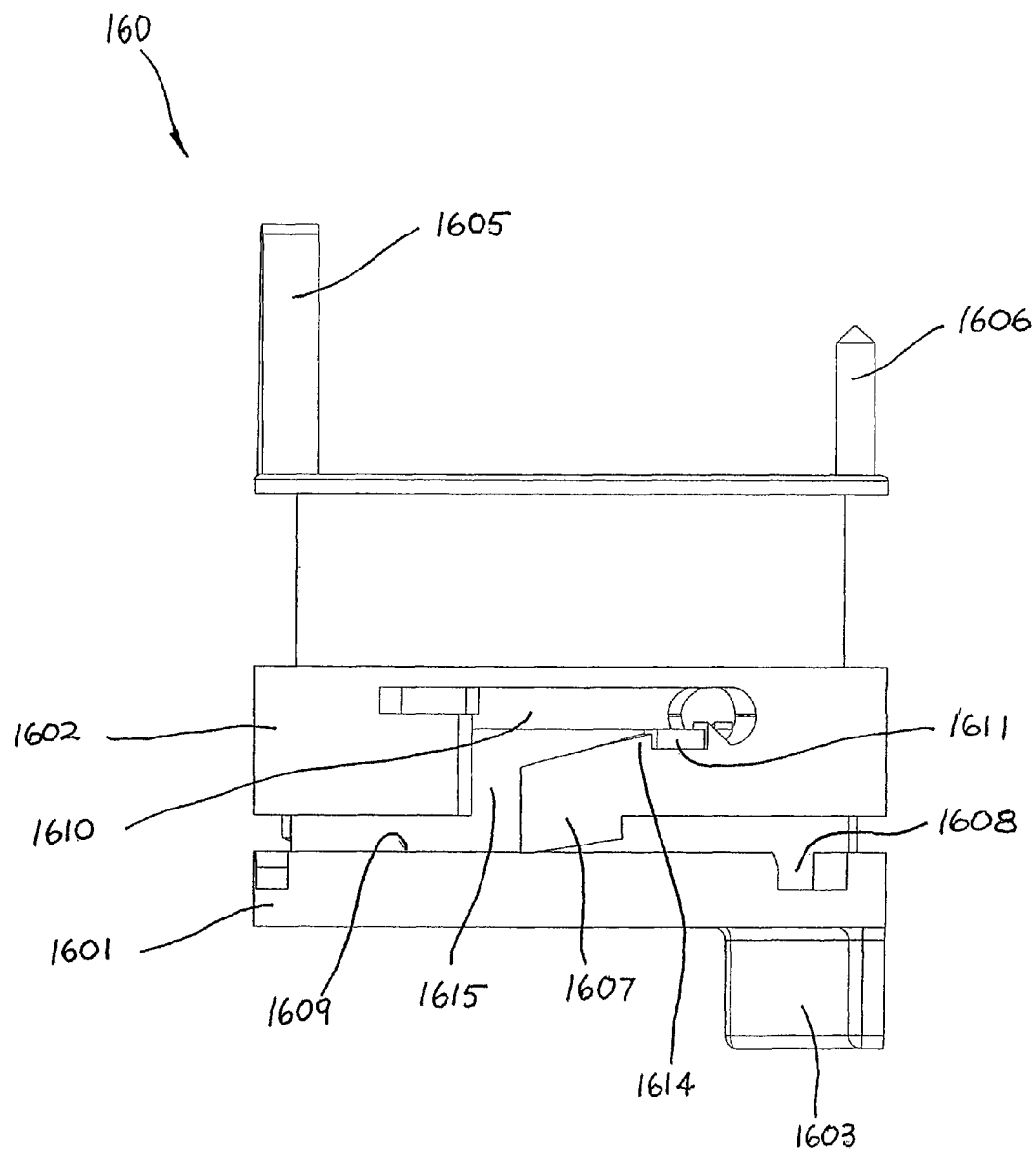
FIG. 14 is a side elevation view of the re-use prevention mechanism of FIG. 13, shown with the first and second collars engaged in the first position.
Figure 15:
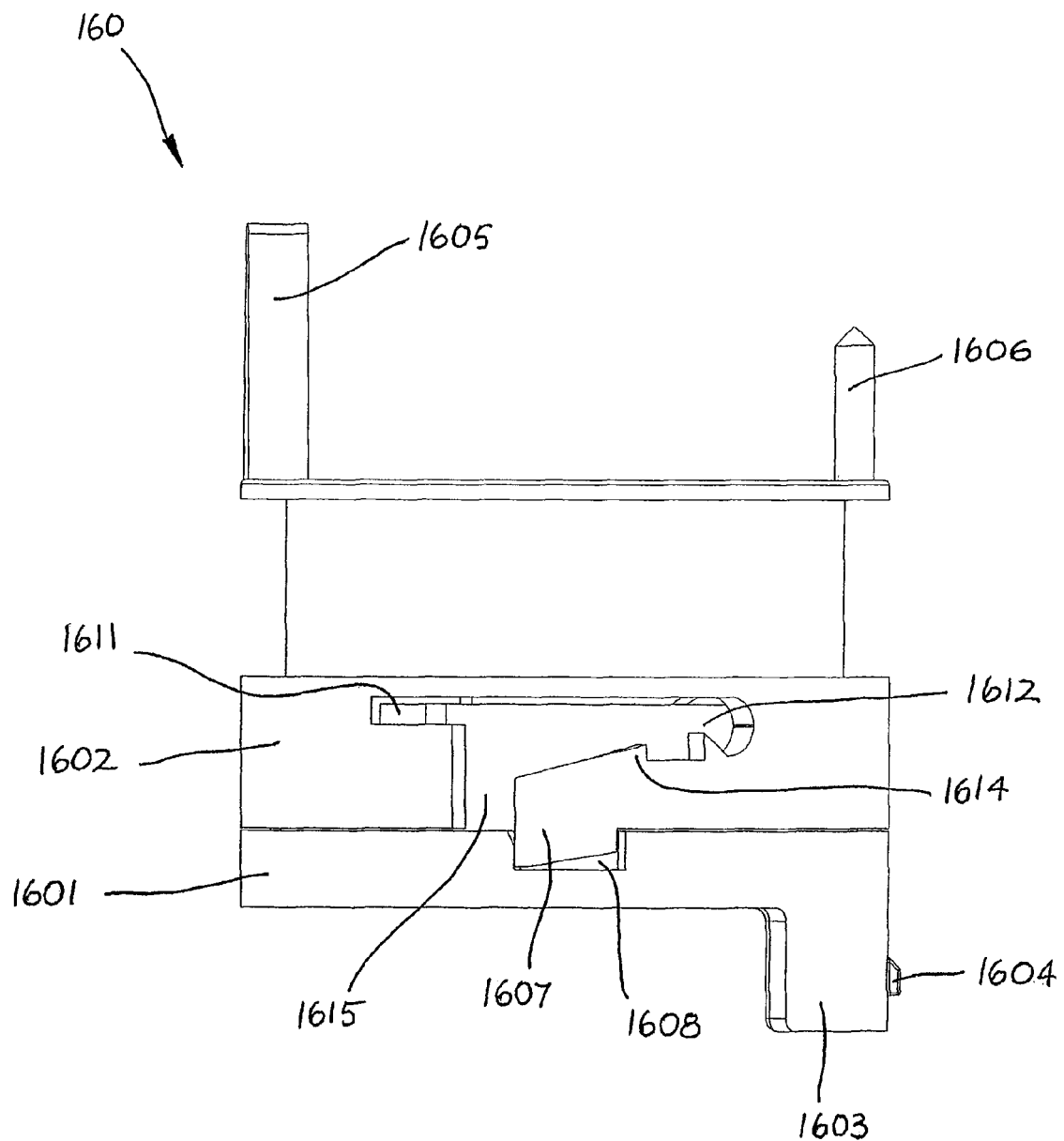
FIG. 15 is a side elevation view of the re-use prevention mechanism of FIG. 13, shown with the first and second collars engaged in the second position.

Returning to FIG. 11, a re-use prevention mechanism 160 is captivity retained within the coupling sleeve 1304 of the blade 130. When the laryngoscope 110 is in use, the re-use prevention mechanism 160 is located between the blade 130 and the handle 120, as can be seen in FIG. 12. The mechanism 160 includes first 1601 and second 1602 interengageable collars, which are shown in detail in FIGS. 13 to 15. The collars 1601 and 1602 are rotatable relative to one another about the longitudinal axis 1201 between a first position, as shown in FIG. 14, and a second position, as shown in FIG. 15. The collars 1601 and 1602 are also rotatably lockable relative to one another in the first and second positions. Moreover, the collars 1601 and 1602 permanently lock together when in the second position.

Figure 13:
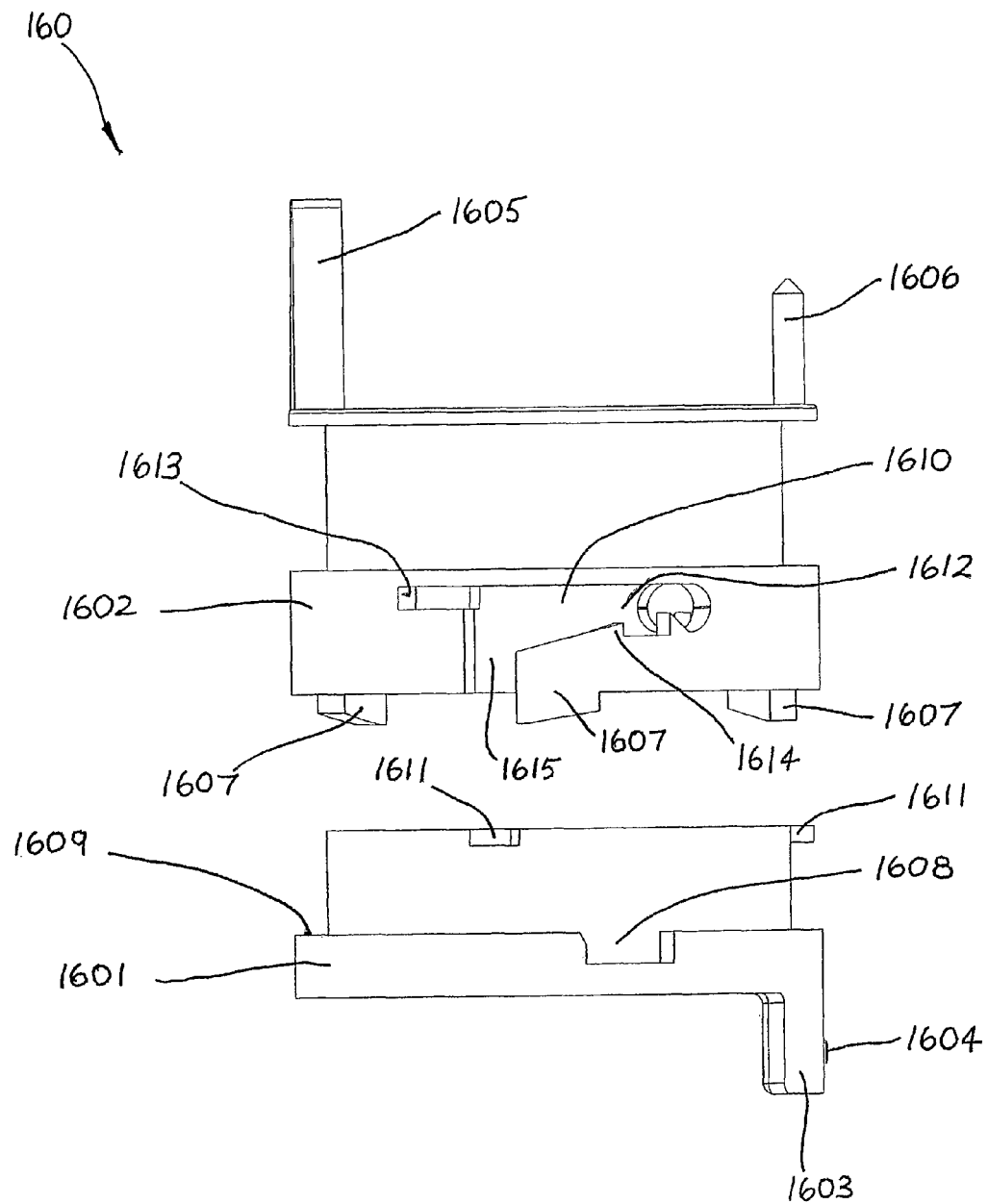
FIG. 13 is an enlarged side elevation view of the re-use prevention mechanism of the laryngoscope system of FIG. 1, shown with the first and second collars disengaged.
Figure 16:
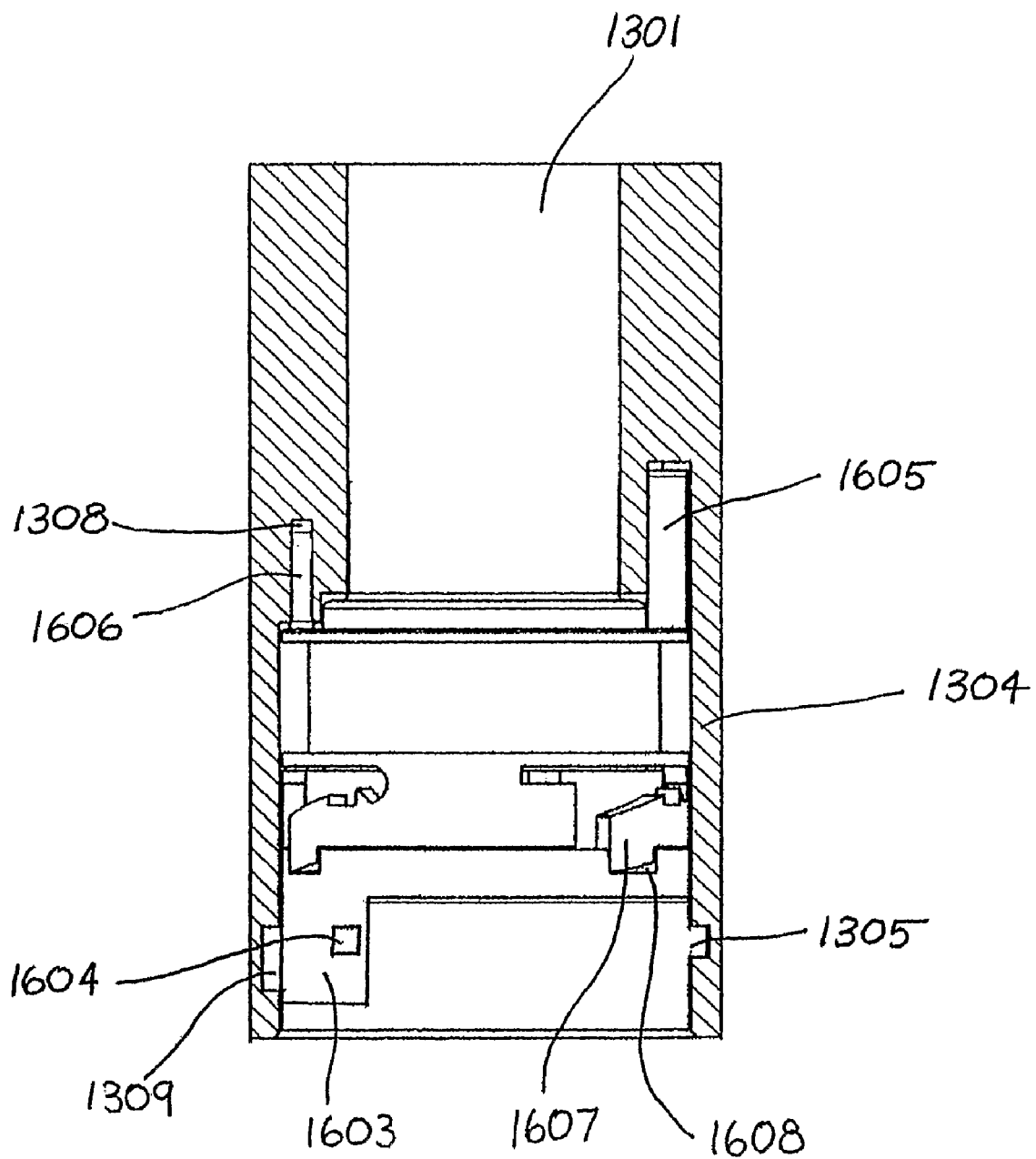
FIG. 16 is a longitudinal section view through the proximal end of the blade of FIG. 14, taken after the blade has been removed from the handle and showing the blocking tab in a blocking position.

Referring to FIG. 13, the first collar 1601 includes a blocking portion in the form of a longitudinally extending generally rectangular tab 1603. When the collars 1601 and 1602 are in the first position, as shown in FIGS. 9, 11 and 14, the blocking portion aligns with and engages the recess 1207 in the abutment surface 1206. This engagement rotationally locks the first collar 1601 to the handle 120, and thereby locks the blade 130 to the handle 120 if the first 1601 and second 1602 collars are rotationally interlocked in one of the first and second positions. Engagement of the blocking portion 1603 with the recess 1207 also permits sufficient longitudinal engagement of the blade 130 with the handle 120 to allow the locking lugs 1210 and locking flanges 1309 to engage, as shown in FIG. 12. When in a blocking position, as shown in FIG. 16, the tab 1603 is engageable with the abutment surface 1206 of the handle 120 to prevent the blade 130 from being reused by limiting the extent of longitudinal engagement of the blade 130 with the handle 120 and thereby preventing engagement of the locking lugs 1210 and locking flanges 1309. As shown in FIG. 11, a retaining lug 1604 also extends radially outwardly from a peripheral surface of the blocking tab 1603 for engagement with the retaining groove 1305 in the coupling sleeve 1304 of the blade 130 to captivity retain the reuse prevention mechanism 160 within the coupling sleeve 1304.

Referring again to FIG. 13, the second collar 1602 includes an actuating member in the form of a resilient biasing finger 1605, which extends from the second collar 1601 longitudinally outwardly away from the handle 120. As shown in FIG. 10, the biasing finger 1605 is operable between the abutment portion 1307 of the blade 130 and the blocking tab 1603 for resiliently biasing the blocking tab 1603 rotationally about the longitudinal axis 1201, so as to move the blocking tab 1603 into the blocking position, as shown in FIG. 16, upon disconnection of the blade 130 from the handle 120. When the blocking tab 1603 is in the blocking position, re-connection of the blade 130 to the handle 120 is prevented.

As can be seen in FIG. 13, the second collar 1602 also includes a locking pin 1606. As shown in FIGS. 11 and 12, the locking pin 1606 is engageable with the locking aperture 1308 in the blade 130 to prevent relative rotation of the first collar 1601 and the blade 130 when the pin 1606 and aperture are engaged. The locking pin 1606 is adapted to fail if a predetermined torque is applied between the blade 130 and the handle 120. The locking pin 1606 is designed to withstand a torque sufficient to apply a shear force to the pin of between around 5 N and around 100 N, and more preferably between around 30 N and around 70 N. However, in a particularly preferred embodiment, the pin 1606 is adapted to fail if a torque sufficient to generate a shear force of around 45 N is applied.

Referring again to FIG. 13, the second collar 1602 also includes three circumferentially spaced locking detents 1607. The first collar 1601 includes three corresponding notches 1608. The locking detents 1607 are engageable with the notches 1608 for locking the first 1601 and second 1602 collars against relative rotation about the longitudinal axis 1201. The locking detents 1607 engage the notches 1608 when the collars 1601 and 1602 are in the second position, as shown in FIG. 15. However, as shown in FIG. 14, when not engaged with the notches 1608, the locking detents 1607 resiliently engage a radially outwardly extending circumferential flange 1609 of the first collar 1601 and thereby resiliently bias the first 1601 and second collars 1602 longitudinally away from one another.

Again, referring to FIG. 13, three circumferential slots 1610 are provided in the second collar 1602 and are engageable by corresponding guide projections 1611 extending radially outwardly from the first collar 1601. The slots 1610 and guide projections 1611, as with the detents 1607 and notches 1608, are also unevenly circumferentially spaced. A first end 1612 of each of the slots 1610 defines the first relative position of the first 1601 and second 1602 collars, as shown in FIG. 14, and a second end 1613 of the slots 1610 defines the second relative position of the collars 1601 and 1602, as shown in FIG. 15. A stop member 1614 is provided at the first end 1612 of each of the slots 1610 and is engageable by the corresponding guide projection 1611 to retain the collars 1601 and 1602 in the first position. The guide projections 1611 can be disengaged from the corresponding stop members 1614 by applying a longitudinal compressive force between the blade 130 and the handle 120 to cause the guide projections 1611 to ride over the stop members 1614 against the resilient bias of the locking detents 1607.

As can be seen in FIG. 13, three longitudinally extending openings 1616 extend from an inner longitudinal end 1616 of the second collar 1602. Again, the openings 1616 are unevenly circumferentially spaced about the second collar 1602. Each of the openings 1616 extends into a corresponding one of the three slots 1610. The guide projections 1611 are each longitudinally slidably engageable with a corresponding one of the longitudinal openings 1616 to facilitate interengagement of the first 1601 and second 1602 collars. The uneven spacing of the openings 1616 and the guide projections 1611 about the second collar 1602 ensures that the first 1601 and second 1602 collars can only be interengaged in a single predetermined relative rotational orientation. It will be appreciated that this predetermined relative orientation corresponds to a predetermined relative rotational location of the blocking portion 1603 and the biasing finger 1605.

Connection of the Blade and Handle

To install the re-use prevention 160 mechanism into the blade 130, the first 1601 and second 1602 collars are connected together in the first position as shown in FIG. 14. The re-use prevention mechanism 160 is then longitudinally inserted into the coupling sleeve 1304 of the blade 130 and is retained axially by engagement of the retaining lug 1604 and retaining groove 1304 and retained rotationally by engagement of the locking pin 1606 and locking aperture 1308, as shown in FIG. 11. When the collars 1601 and 1602 are in the first position and with the retaining lug 1604 and retaining groove 1304 engaged, the blocking portion 1603 is correctly aligned for engagement with the recess 1207 of the handle 120. In a preferred form, the blade 130 is supplied with the re-use prevention mechanism 160 pre-installed, as shown in FIG. 11.

To connect the blade 130 to the handle 120, the distal end of the handle 120 is longitudinally inserted into the coupling sleeve 1304 and, if required, the handle 120 is rotated about the longitudinal axis 1201 until the recess 1207 aligns with the blocking tab 1603. With the recess 1207 and blocking tab 1603 aligned, a longitudinal compressive force is applied between the blade 130 and the handle 120 to cause the blade 130 to be pressed fully on to the handle 120, whereupon the blocking tab 1603 fully engages the recess 1207 and the guide projections 1611 are caused to ride over the corresponding stop members 1614, and then the handle 120 is rotated anticlockwise with respect to the blade 130 to move the collars 1601 and 1602 into the second position, as shown in FIG. 12. Engagement of the locking pin 1606 with the locking aperture 1308 and the blocking tab 1603 with the recess 1207 secure the first 1601 and second 1602 collars respectively to the blade 130 and handle 120 during rotation between the first and second positions.

During rotation of the blade 130 relative to the handle 120 between the first and second positions, the locking lugs 1210 and locking flanges 1309 engage to axially secure the blade 130 to the handle 120 in the second position, as shown in FIG. 12. Also, when the second position is reached, the locking detents 1607 and notches 1608 engage to secure the first 1601 and second 1602 collars against relative rotation. Also, engagement of the guide projections 1611 with the slots 1610 locks the collars 1601 and 1602 together axially. Accordingly, in the second position, the collars 1601 and 1602 are permanently locked together. With the collars 1601 and 1602 so secured, engagement of the blocking tab 1603 with the recess 1207 and the locking pin 1606 with the locking aperture 1308 rotationally locks the blade 130 to the handle 120.

It will be appreciated that during connection of the blade 130 to the handle 120, the tip of the blade 130 is isolated from the handle 120 to reduce the probability of contamination of the blade 130 by the handle 120. This situation is contrasted to that of known laryngoscopes, where it is necessary for the blade tip to be placed very close to the handle prior to align the coupling components of the blade and handle prior to rotating the blade upwardly with respect to the handle to lock the blade onto the handle.

Disconnection of the Blade and Handle

To disconnect the blade 130 from the handle 120, the handle 120 is rotated clockwise with respect to the blade 130, about the longitudinal axis 1201. A predetermined torque must be applied between the blade 130 and the handle 120 to cause shear failure of the locking pin 1606 and thereby allow the handle 120 to rotate relative to the blade 130. Once the pin 1606 has failed, the handle 120 will rotate sufficiently relative to the blade 130 to disengage the locking lugs 1210 and flanges 1309. Also, as the handle 120 is rotated, the biasing finger 1605 is deformed against the abutment portion 1307 of the coupling sleeve 1304, as shown in FIG. 10, such that when the distal end 1203 of the handle 120 is longitudinally removed from the coupling sleeve 1304, the biasing finger 1605 resiliently rotates the blocking tab 1603 in an anti-clockwise direction relative to the blade 130 and into a blocking position as shown in FIG. 16. As discussed above, with the blocking tab 1603 in the blocking position, if a user attempts to re-connect the blade 130 to the handle 120, the blocking tab 1603 engages the annular abutment surface 1206 of the handle 120 to prevent the extent of longitudinal engagement of the handle 120 and blade 130 required to allow the locking lugs 1210 and flanges 1309 to engage.

Alternative Embodiments

It will be appreciated by those skilled in the art that the claimed invention may be embodied in many other forms. Some alternative embodiments are provided below by way of example only:

- the re-use prevention mechanism may be connected to the handle, rather than to the blade;
- the actuating member may be connected to the blade or the handle rather than to either of the collars and may engage the collars, rather than being connected to one of the collars and engaging the blade or the handle;
- the biasing finger may act between the handle and the blocking portion, rather than between the blade and the blocking portion.

As will be appreciated, the several examples of alternative embodiments listed above are by no means exhaustive, and those skilled in the art will understand that many additional alternative embodiments of various components of the illustrated laryngoscope may be employed within the scope of the invention. Also, while the invention has been described with reference to a laryngoscope, it can also be used in other medical instruments, such as endoscopes and catheters, or indeed, in non-medical devices where hygiene is important, for example in electric toothbrushes with disposable heads, to reduce the incidence of cross-infection or contamination resulting from re-use of disposable parts.

The invention claimed is:

1. A re-use prevention mechanism for an apparatus having a reusable part and a single-use disposable part connectable to the reusable part, the re-use prevention mechanism comprising:
    a blocking portion disposed, during the single-use, between the connected disposable part and the reusable part, the blocking portion being adapted to engage a recess in the reusable part to rotationally lock the disposable part to the reusable part; and
    an actuating member operable between the blocking portion and one of the disposable part and the reusable part for moving the blocking portion into a blocking position upon disconnection of the disposable part from the reusable part;
    wherein, in the blocking position, the blocking portion engages an abutment surface on one of the disposable part and the reusable part if a user attempts to reconnect the disposable part to the reusable part and thereby prevents re-connection of the disposable part to the reusable part.

2. A mechanism according to claim 1, wherein the actuating member is operable between the blocking portion and the disposable part.

3. A mechanism according to claim 1, including first and second interengageable collars connectable with one of the disposable part and the reusable part, the collars being rotatably lockable to one another in first and second relative rotational positions, wherein the blocking portion extends from one of the collars, and wherein in the first position if a user attempts to connect the disposable part to the reusable part, the blocking portion engages the recess, and wherein in the second position if a user attempts to connect the disposable part to the reusable part, the blocking portion engages the abutment surface.

4. A mechanism according to claim 3, wherein the collars are connected to the disposable part.

5. A mechanism according to claim 3, wherein the blocking portion extends from the first collar.

6. A mechanism according to claim 5, wherein a locking pin extends from the second collar for engagement with a corresponding locking aperture in the disposable part to prevent relative rotation of the first collar and the disposable part when the pin and aperture are engaged.

7. A mechanism according to claim 6, wherein the locking pin is adapted to fail if a torque above a predetermined level is applied between the disposable part and the reusable part.

8. A mechanism according to claim 3, wherein the actuating member takes the form of a resilient biasing finger extending longitudinally outwardly, away from the reusable part, from the second collar for engagement with an abutment portion on the disposable part to resiliently bias the second collar rotationally, about a longitudinal axis of the reusable part, with respect to the disposable part when the biasing finger is deformed against the abutment portion.

9. A mechanism according to claim 8, wherein the resilient biasing finger is deformed against the abutment portion when the disposable part is rotated relative to the reusable part to disconnect the disposable part from the reusable part.

10. A mechanism according to claim 3, wherein the second collar includes a plurality of locking detents engageable with a corresponding plurality of notches in the first collar for locking the first and second collars against relative rotation about a longitudinal axis of the reusable part when the collars are in the second position.

11. A mechanism according to claim 3, wherein the collars permanently lock together when moved into the second position.

12. A mechanism according to claim 3, wherein the second collar includes a plurality of circumferential slots and the first collar includes a corresponding plurality of radially extending guide projections engageable with the slots, and wherein a first end of each said slot defines the first position and a second end of each said slot defines the second position.

13. A mechanism according to claim 12, including a longitudinally extending opening corresponding to each of said slots, the openings extending from one longitudinal end of the second collar and into said slots, and wherein the guide projections are each longitudinally slidably engageable with a corresponding one of said longitudinal openings to facilitate interengagement of the first and second collars.

14. A mechanism according to claim 13, wherein said slots, said guide projections and said longitudinal openings are unevenly circumferentially spaced about said re-use prevention mechanism, such that said first and second collars can only be interengaged in a single predetermined relative rotational orientation.

15. A mechanism according to claim 3, wherein, with the collars in the first position, the disposable part is axially slidable onto a distal end of the reusable part, and wherein, when the disposable part is engaged with the distal end of the reusable part and the disposable part is rotated relative to the reusable part in a predetermined direction, the collars are moved into the second position and the disposable part is rotationally locked to the reusable part.

16. A mechanism according to claim 15, wherein, with the disposable part rotationally locked to the reusable part, if a user applies a torque above a predetermined level between the disposable part and the reusable part, a component of the mechanism fails, to allow the disposable part to rotate relative to the reusable part.

17. A mechanism according to claim 1, wherein the disposable part is a laryngoscope blade and the reusable part is a laryngoscope handle.

18. A medical device comprising:
   an elongate reusable part defining a longitudinal axis;
   a disposable part for connection to the reusable part by engaging the disposable part with a longitudinal end of the reusable part and rotating the disposable part relative to the reusable part about the longitudinal axis; and
   a re-use prevention mechanism operable such that the disposable part is single-use connectable to the reusable part, the re-use prevention mechanism comprising:
      a blocking portion disposed, during the single use, between the connected disposable part and the reusable part, the blocking portion being adapted to engage a recess in the reusable part to rotationally lock the disposable part to the reusable part; and
      an actuating member operable between the blocking portion and one of the disposable part and the reusable part for moving the blocking portion into a blocking position upon disconnection of the disposable part from the reusable part;
      wherein, in the blocking position, the blocking portion engages an abutment surface on one of the disposable part and the reusable part if a user attempts to reconnect the disposable part to the reusable part and thereby prevents re-connection of the disposable part to the reusable part.

19. A medical device according to claim 18, wherein the reusable part takes the form of a handle and the disposable part is adapted for insertion into a patient.

20. A disposable laryngoscope apparatus for use with a laryngoscope handle defining a longitudinal axis, said laryngoscope apparatus comprising:
   a laryngoscope blade for connection to the handle by engaging the blade with a longitudinal end of the handle and rotating the blade part relative to handle about the longitudinal axis; and
   first and second interengageable collars connectable with one of the blade and the handle, the collars being rotatably lockable to one another in first and second relative rotational positions; wherein
   the first collar comprises a blocking portion extending therefrom and disposed, in use, between the blade and the handle, wherein when the blade is engaged with the handle, the blocking portion is adapted to engage a recess in the handle to rotationally lock the blade to the handle and wherein in the first position if a user attempts to connect the blade to the handle, the blocking portion engages the recess; and
   the second collar comprises an actuating member extending therefrom and operable between the blocking portion and one of the blade and the handle for moving the blocking portion into a blocking position upon disconnection of the blade from the handle, wherein when in the blocking position, the blocking portion engages an abutment surface on one of the blade and the handle if a user attempts to reconnect the blade to the handle to thereby prevent re-connection of the blade to the handle, and wherein in the second position if a user attempts to connect the blade to the handle, the blocking portion engages the abutment surface.

* * * * *